US00PP19246P2

(12) United States Plant Patent
Peterson et al.

(10) Patent No.: US PP19,246 P2
(45) Date of Patent: Sep. 16, 2008

(54) GRAPEVINE-"'CHISAGO'"

(50) Latin Name: ***Vitis* spp. hybrid**
Varietal Denomination: Chisago

(75) Inventors: Kevin Peterson, Chisago City, MN (US); Kyle Peterson, Crystal, MN (US)

(73) Assignee: Winehaven, Inc., Chisago City, MN (US)

( * ) Notice: Subject to any disclaimer, the term of this patent is extended or adjusted under 35 U.S.C. 154(b) by 244 days.

(21) Appl. No.: 11/305,770

(22) Filed: Dec. 16, 2005

(51) Int. Cl.
*A01H 5/00* (2006.01)

(52) U.S. Cl. ..... Plt./205
(58) Field of Classification Search ..... Plt./205
See application file for complete search history.

(56) References Cited

U.S. PATENT DOCUMENTS

PP4,928 P 11/1982 Swenson
PP5,771 P 7/1986 Swenson
PP6,159 P 4/1988 Reisch et al.
PP6,160 P 4/1988 Reisch et al.
PP7,860 P 5/1992 Reisch et al.
PP11,012 P 7/1999 Reisch et al.
PP13,309 P2 12/2002 Clark et al.
PP14,617 P3 3/2004 Luby et al.
PP16,115 P3 11/2005 McKenry

OTHER PUBLICATIONS

Minnesota Grape Growers Association: Cold Hardy Grape Varieties, www.mngrapes.org/varities.html.

"A Word About Cold Hardy Hybrids From Minnesota", Vineyard & Winery Management, Sep./Oct. 2005.

*Primary Examiner*—Wendy C. Haas
(74) *Attorney, Agent, or Firm*—Patterson, Thuente, Skaar & Christensen, P.A.

(57) ABSTRACT

The invention is a new and distinct variety of grapevine designated 'Chisago', which has a combination of outstanding wine quality, vigor, disease resistance, and cold hardiness.

4 Drawing Sheets

Latin name of the genus and species: Botanical classification: *Vitis* spp. hybrid.
Variety denomination: Variety denomination: 'Chisago'.

BACKGROUND OF THE INVENTION

Minnesota has a summer thermal accumulation similar to that of the best grape growing regions of the world. However, the state's mid-continental climate yields exceptionally cold winters that create challenges for Minnesota's emerging grape wine industry. At present, less than 20 wineries exist in Minnesota, extending from southern Minnesota to just south of the Canadian border. Many of these wineries produce non-grape wines from honey, rhubarb, raspberries, and the other fruit. However, several Minnesota wineries are currently managing substantial vineyard tracts. A few wineries have even received awards for wines produced by these vineyards at top international wine competitions in New York and California.

Despite some success, grape growing in Minnesota is Fraught with difficulties. Most European grape varieties that are grown in Minnesota, and even many "French-American hybrid" wine varieties, require protection if they are to survive the frigid winters — especially in northern Minnesota. This is usually done by removing vines from the trellises and bending them to the ground in early November, then covering the vine with soil or straw.

Although covering vines effectively insulates them from cold winter temperatures, there are a number of problems that make this practice less than satisfactory. Of primary concern is the greatly increased labor cost, which is generally prohibitive and makes it quite difficult for Minnesota vineyards to operate profitably. However, logistical challenges exist as well. For example, the trunks of the vine may break due to the fact that they become less pliable as they grow larger in diameter. If the vine does not break, fungi and bacteria may infiltrate the vine through small "stress cracks" in the trunk, causing disease. Rodents commonly feed on the trunks and canes as they lay on the ground the winter, further injuring the vine. If the vine survives the winter, great care must be taken to avoid damaging the buds when the vines are uncovered during the spring. Accordingly, for grapevines to be of high commercial value to vineyards in northern regions, it is nearly essential for varieties to be hardy enough to remain on the trellises throughout the winter months without removal and winter covering.

Fortunately, there exists good sources of tolerance to cold hardiness for breeding purposes, i.e. *Vitis riparia* and *vitis Labrusca.* These hardy grapes have a flavor that is acceptable in table wines. However, they are too high in acid and too unproductive to use on their own.

Some of the hardiest known wine grape varieties, 'Sabrevois' (ES 2-1-9), and 'Frontenac' (MN 1047), have demonstrated hardiness to at least −35° F. (about −37.2°C.) in Chisago City, Minn. At this location, the present variety has proven that it is at least as winter hardy as these known varieties. The present variety also presents a wide variety of additional distinguishing characteristics including vigor, productivity, resistance to disease and pests, size of fruit, coloration, and flavor, hereinafter set forth in detail.

BRIEF SUMMARY OF THE INVENTION

The present invention relates to a new and distinct cultivar of grape plant botanically known as *Vitis* spp. Hybrid 'Chisago', referred to hereinafter by its cultivar name, 'Chisago'. The 'Chisago' grapevine has a unique combination of hardiness, vigor, disease resistance, and wine quality not found in existing grape varieties. Fruit of 'Chisago' can be fermented to produce red wine having a deep red color and desirable aromas of cherry, currant, raspberry, and blackberry. The wine lacks "foxy" aromas typically associated with *V. labrusca*. It also lacks herbaceous aromas that are commonly associated with *V. riparia*. The fruit at harvest is usually slightly lower in sugar and higher in acidity than wines associated with *V. vinifera*.

When grown in east central Minnesota, the plants of 'Chisago' are extremely vigorous and winter hardy to at least −40° F. (−40° C.). The vines are somewhat resistant to herbicide injury and moderately susceptible to foliar phylloxera (*Daktulospahira vitifoliae*) damage. The disease black rot, caused by *Guignardia bidwellii,* has been observed sporadically and at low levels on the leaves, but not on the fruit. Downy mildew, caused by *Plasmopara viticola,* has been observed at moderate levels on the foliage, but has not been seen on the fruit. Powdery mildew disease, caused by *Uncinula necator,* has been seen at low levels on the foliage, but not on the fruit.

'Chisago' vines set a moderate to heavy crop load from year to year, that varies with pruning technique. The fruit are borne on loose, medium sized clusters. The berries are medium sized and blue-black in color with a waxy bloom at maturity. The berries resist prematurely separating from the cluster, and have consistently been observed hanging on the vine well after harvest, and more than a month after a hard freeze. The berries have not been observed to split, even under wet conditions in the autumn.

BRIEF DESCRIPTION OF THE DRAWINGS

The accompanying color photographs show characteristics of 'Chisago' grown under typical field conditions in east central Minnesota. The photographs depict the color features as true as is reasonably possible.

DETAILED BOTANICAL DESCRIPTION

Figure 1:
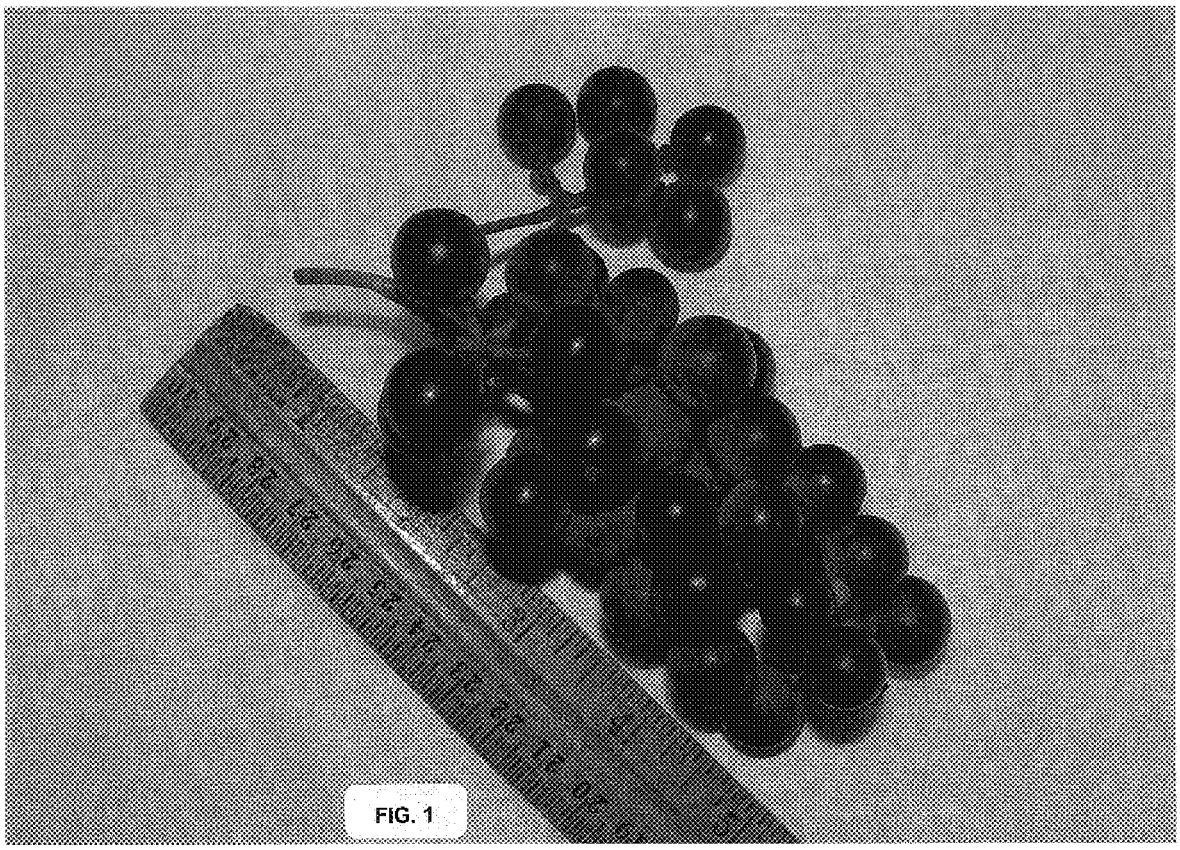
FIG. 1. shows a close-up photo of a fruit cluster of 'Chisago' in mid September.
Figure 2:
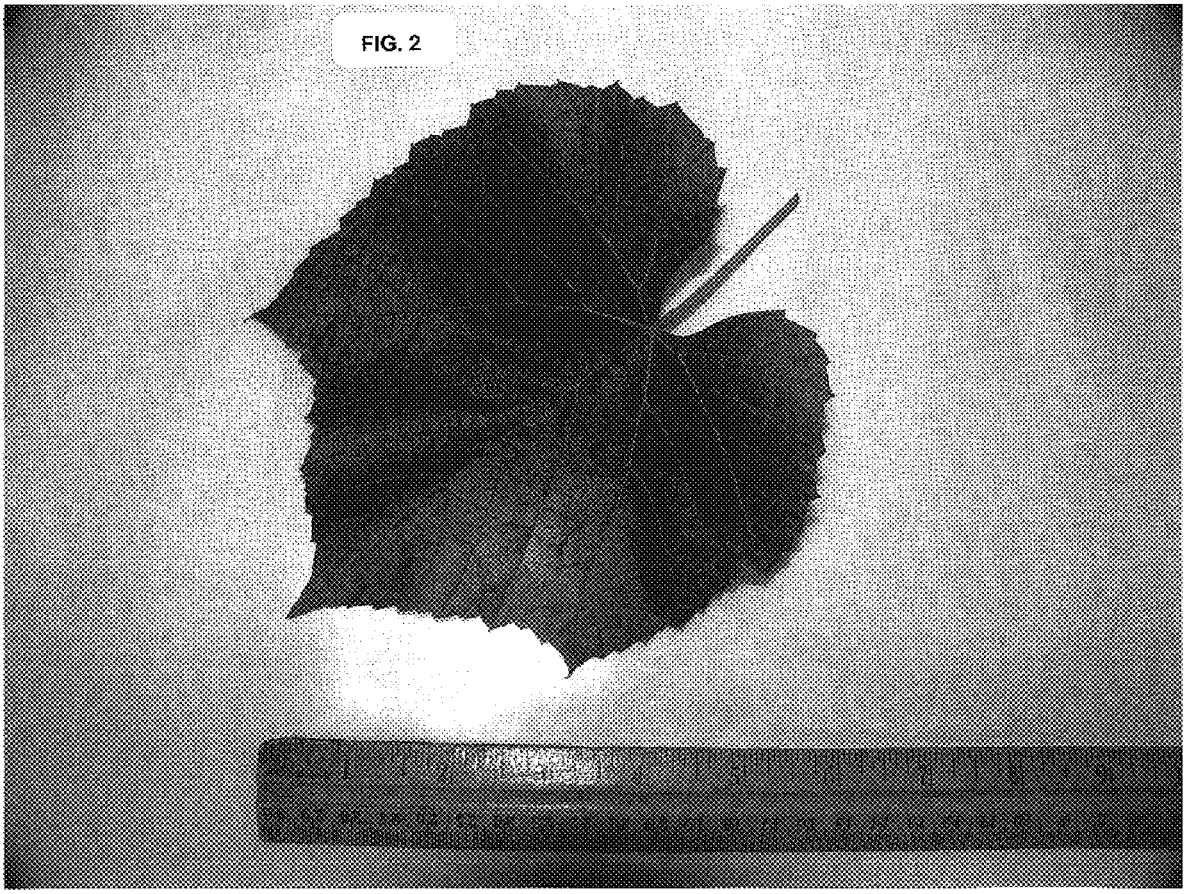
FIG. 2. shows a mature leaf, upper surface in mid September.
Figure 3:
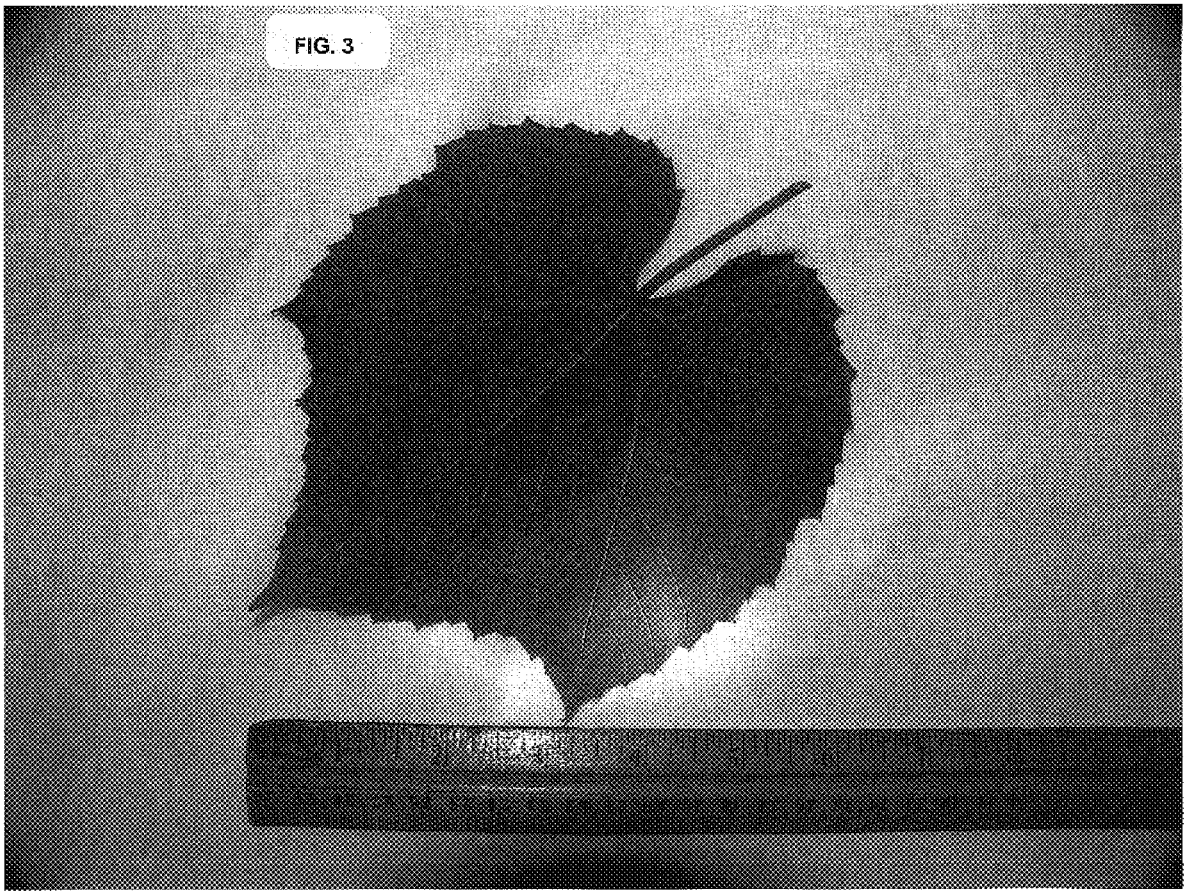
FIG. 3. shows a mature leaf, lower surface in mid September.
Figure 4:
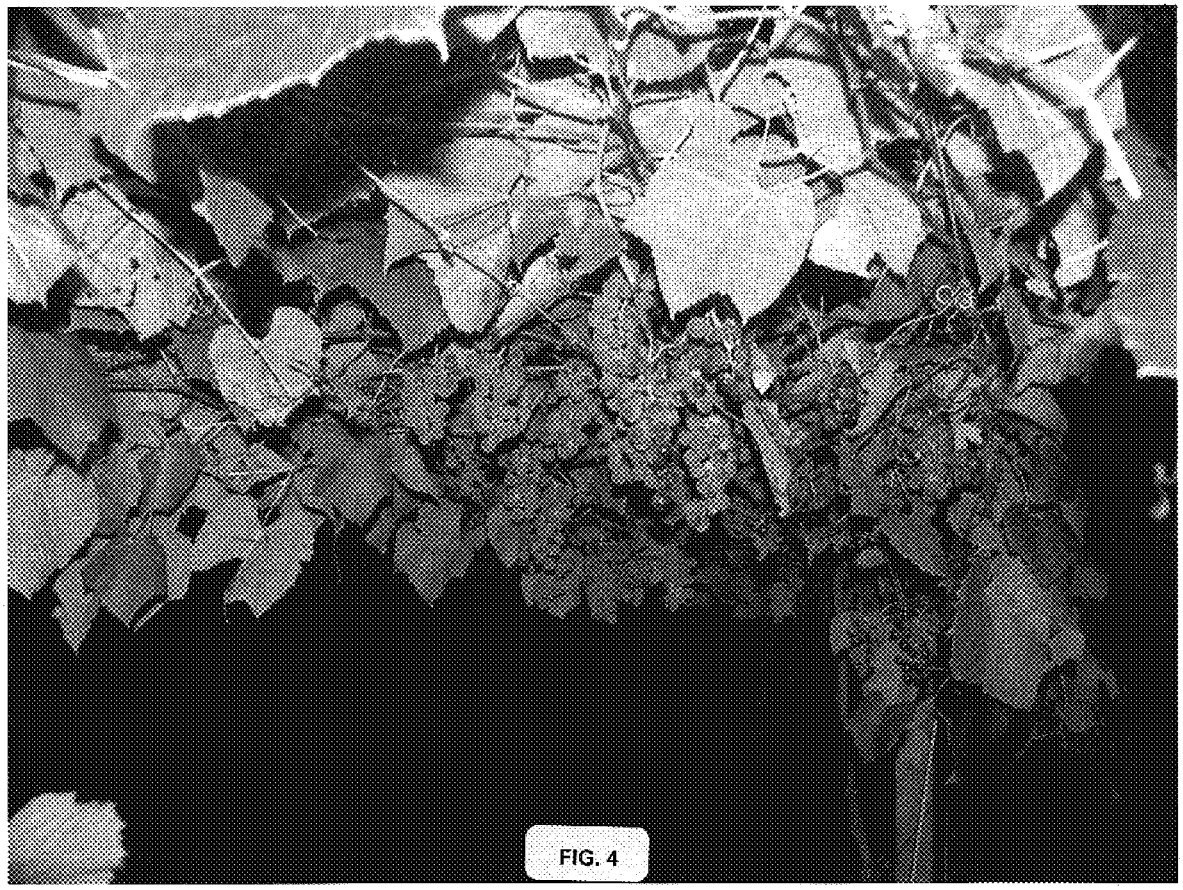
FIG. 4. shows a mature vine before harvest in mid September.

'Chisago' was selected for its combination of good winter hardiness, vigor, disease resistance and overall suitability as a red wine grape. It arose as a result of the inventors' grape breeding program to develop commercially viable wine grape varieties to complement non-grape wines produced at their winery.

The grapevine of the new variety was discovered by the inventors among a number of cross combinations in the breeding program. The breeding program produced several test seedlings which were evaluated for their characteristics related to a variety of considerations including, but not limited to, hardiness, vigor, disease resistance, and commercial potential as a wine grape variety. The grapevine was discovered in a controlled cross of the grape 'St. Croix' (U.S. Plant Pat. No. 4,928) ('ES114' times 'Seyval') times ('Minn 78' times 'Seneca'), which was the female parent, and the grape 'Swenson Red' (not patented) ('Minn 78' times 'Seibel 11803'), which was the male parent. The inventors have identified the present variety as 'KP 13' and selected the name 'Chisago' therefor.

The inventors have asexually reproduced the present variety at WineHaven Winery and Vineyard in Chisago City by means of cuttings, and have carefully observed the variety for approximately 15 years. The following data pertains to vines grown in Chisago City, Minn. Alphanumeric color designations refer to values based on the 1995 R.H.S. Color Chart published by The Royal Horticultural Society, London, England. Many of the descriptors are based on those set forth by the International Board for Plant Genetic Resources in collaboration with the Office Internationale de la Vine et du Vin (OIV) and the International Union for the Protection of New Varieties of Plants.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

Botanical Classification: Cultivar of *Vitis* with ancestry tracing to several species including *V. labrusca* and *V. riparia*.
Parentage: 'St. Croix' (female), 'Swenson Red' (male).

The progeny of 'Chisago' are stable and reproduced true to type in successive generations. 'Chisago' has perfect flowers containing extended stamens with anthers having viable pollen. When ripe, the berries of 'Chisago' are blue-black in color 202A with 98D bluish bloom.

The present invention has been shown to be winter hardy to at least −40° F. (−40° C.) in Chisago City. By way of comparison, the grapevine 'Chisago' is slightly more winter hardy than its parents. For example, 'St. Croix' is hardy to about −32° F. (about −35.6° C.). 'Swenson Red' is hardy to about −30° F. (about −34.4° C.). The values presented below are means (with ranges in parentheses) from vines observed in the 2005 growing season.

VINE

Size and Vigor:

*Size.*—Vines are large and grow best in rows with 8 feet (about 2.4 meters) of spacing between vines.

*Vigor.*—Vigorous — new vines propagated from cuttings were established in a greenhouse on Mar. 1st, 2005 and transplanted to a new vineyard located in Chisago City, Minn. on May 17, 2005. Over 75% of the new vines grew at least 4 feet (about 1.2 meters) by Sep. 1$^{st}$, 2005. Applicants have also found it beneficial to train the vine to grow only a single trunk to reduce crowding due to plant vigor in a given growing season. Productive capacity: in vineyards located in Chisago City, Minn., 'Chisago' vines in experimental plots have consistently produced 5.46 Kg/vine or the equivalent of 3.6 tons of ripe fruit per acre.

Canes: Canes are medium length 5' (about 152 cm) to 10' (about 305 cm). Color of canes: brown; 175A, 175B, 175C. Thickness of canes: medium. Average width at node is 0.5 inch (about 15.2 cm). Diameter at base: 3.1 inches (about 7.9 cm) to 4.7 inches (about 11.9 cm). Diameter at midpoint: 1.9 inch (about 4.8 cm) to 3.5 inch (about 8.9 cm).

Shoots:

Length of shoots: medium to long, approximately 6.5 inches (about 16.5 cm). Internode length: approximately 3 inches (about 76 mm). Width at node — approximately 0.5 inches (12.7 mm). Shape — circular to slightly flat. Diameter — approximately 10 mm. Contour — smooth. Color of shoots 144A, 144B, yellow-green. Growing tip: generally hang over wires.

Tendrils: Length of tendrils: 4 inches (10.16 mm) to 7 inches (17.78 mm). Texture of tendrils: smooth. Color of tendrils 166A, 166C.

Buds: Shape of buds: pointed. Size of buds: medium, approximately 4 mm times 5 mm. Position of buds — markedly held out at approximately 45 degree angle. Cane bud fruitfulness — basal most fruitful. Bud color: 166B. Bud break: near Chisago City along the St. Croix River Valley of east-central Minnesota, bud break is during the middle of May.

Trunk: Trunk: bark texture — moderately flaky, small vertical segments approximately 0.40 cm×6.0 cm. Bark color: striated, 201C and 201D.

LEAVES

Ten representative mature leaves from different vines were examined during the 2004 and 2005 growing seasons. The leaves were pressed and dried for later analysis. The values presented below are ranges from collections during September of each year.

*Length of mature leaf.*—4 inches (101.6 mm) to 7 inches (177.8 mm). Width of mature leaf — 3.5 inches (88.9 mm) to 6.5 inches (165.1 mm). Shape of blade — oval. Number of lobes — 3. Anthocyanin coloration of main veins on the upper side of the blade — wery weak. Mature leaf profile -flat. Blistering surface of blade upper surface — absent. Leaf blade tip — in the plane of the leaf. Undulation of margin — slight. Undulation of blade between main and lateral veins — absent. Shape of teeth — both sides convex. General shape of petiole sinus — slightly open. Tooth at petiole sinus — absent. Petiole sinus limited by veins — absent. Shape of upper lateral sinus — lobes slightly overlapping. Autumn coloration of leaves — near grayed-yellow 162A, near Yellow-green 153D. Coloration is slow to develop. Normally frost kills leaves before extensive color change. Texture of upper surface of leaf — smooth. Texture of lower surface of leaf — rough. Length of petiole: 4 inches (101.6 mm) to 5 inches (127 mm). Shape of petiole: mostly round. Diameter of petiole — 3.1 mm. Color of petiole: 145A. Color of adaxial leaf surface: 146A, 146B, yellow-green leaf surface. Color of abaxial leaf surface: 146C, yellow-green leaf surface. Pubescence very sparse on main veins abaxial surface and at petiolar junction. Color of leaf veins: 146A, 146B, yellow-green.

FLOWERS

Flower sex: Hermaphrodite. Fragrance: moderately fragrant. Date of bloom: late May when grown in Chisago City, Minn. Date of full bloom: early June when grown in Chisago City, Minn. Type: Fertile, based on use in controlled crosses. Amount of pollen: abundant. Color of pollen: 4B, yellow. Petal shape: cohering at summit and separating at base: 2.5 mm long; 1 mm wide at fused end; reflexed after dehiscence. Shape of cluster: slightly conical. The values presented below are means (with ranges in parentheses) from vines observed during the 2005 growing season. Size of cluster: 8.8 cm long (6.9–11.1); 4.5 cm wide (3.7–7.2). Number of flowers per cluster 118 (92–147). Size of individual flower: 5.2 mm long, 3.9 mm wide. Color of stamen: anther: 162C, grayed yellow. Color of filament: 155A, white. Number of stamen: 5.0 (4–6). Number of pistil: 1 per flower. Length of pistil: 2.4 mm. Color of petal: 145A, yellow-green. Color of sepal: 144A, yellow-green. Color of pistil: 144A, yellow-green.

FRUIT

Maturity: Ripe for commercial harvesting and shipment approximately late September near Chisago City in the St. Croix River Valley of east central Minnesota. Solids — sugar: medium brix (17.1% to 19.6%). Juice pH: (3.10–3.41). Percent titratable acidity: (0.90–1.29%). The values presented below are means (with ranges in parentheses) from fruit observed in the 2005 growing season.

Seeds: Seeds: 3–4 seeds per berry. Seed length: 0.55 mm (0.50–0.55) to 0.63 mm (0.54–0.65). Seed width: 0.33 mm (0.31–0.36) to 0.39 mm (0.35–0.46). Seed weight: 0.020 g. to 0.033 g. Seed Color: 165A, 177A.

Clusters: Generally medium-sized clusters weighing 0.2 pounds (about 91 grams) to 0.5 pound (about 227 grams). Clusters are loose and form a conical shouldered cluster. Cluster length: 10.4 cm (8.1–13.2). Between 40 and 70 berries are included in a typical cluster.

Berries: Berry size is medium and berry form is uniform. For example, the dimension of berries along the longitudinal axis is 0.4375 inch (about 11 mm) to 0.5 inch (12.7 mm). The dimensions of berries along the transverse axis is 0.5 inch (12.7 mm) to 0.75 inch (about 19 mm). Berry weight: 0.07 ounces (about 2 grams) to 0.14 ounces (about 4 grams). Form: round. Skin thickness: Medium. Texture: firm. Tendency to split: none. Color: 202A black with 98D bluish bloom. Color of flesh 63C light pink. Flavor: sweet crisp. Eating quality: good. Use: wine, juice. Shipping and handling qualities: excellent. Keeping quality: After two months in cold storage, still in good appearance.

VINEYARD PERFORMANCE

Based on observations compiled over 10 years (1996–2005). Susceptibility to powdery mildew (*Uncinula necator*): low. Susceptibility to downy mildew (*Plasmopara viticola*): moderate. Susceptibility to black rod (*Guignardia bidwellii*): low. Susceptibility to foliar phylloxera (*Daktulospahira vitifoliae*): moderate. Susceptibility to Crown gall (*Agrobacterium*): no natural infection observed. Susceptibility to phenoxy herbicide drift: low. Winter hardiness: trunks have survived −40° F. (−40° C.). Wood ripening: good.

WINE QUALITY:

Descriptions below are compiled from observations on wine made from 'Chisago' fruit harvested during the 1997–2005 growing seasons.

1. Flavors and aromas: black raspberry, cherry, currant, plum; no herbaceous aroma or very slight *V. labrusca* aroma.
2. Balance: medium body, well balanced when finished with residual sugar.
3. Color: attractive deep red color.
4. Propensity for oxidation: low.
5. Overall quality: excellent.

What is claimed is:

1. A new and distinct variety of grapevine designated 'Chisago' as illustrated and described herein.

* * * * *